Reissued Oct. 28, 1930 Re. 17,846

UNITED STATES PATENT OFFICE

LINWOOD M. BROWN, OF PITTSBURGH, PENNSYLVANIA

STEEL ALLOY

No Drawing. Original No. 1,643,054, dated September 20, 1927, Serial No. 168,228, filed February 14, 1927. Application for reissue filed October 31, 1928. Serial No. 316,345.

My invention relates to steel alloys, and more particularly to the class of steel alloys used in making cutting tools.

One object of the invention is to provide a steel alloy which combines increased strength and toughness with improved hardening, cutting and percussive qualities.

Another object of the invention is the provision of a steel alloy which readily permits of the heat treatment to which such alloy steels are subjected throughout a wide range in temperatures.

With this and other objects in view, the invention consists in a steel alloy of the composition and ranges in proportions hereinafter described and particularly specified in the appended claims.

In making my improved alloy, which preferably will be made in an electric furnace, the alloying elements and approximate ranges in proportions by weight to the various elements in the finished alloy will be substantially as follows—

| | Per cent |
|---|---|
| Carbon | 0.40 to 1.00 |
| Manganese | 0.50 to 1.50 |
| Silicon | 1.50 to 2.50 |
| Molybdenum | 0.15 to 1.50 |
| Vanadium | 0.15 to 0.50 |
| The combined molybdenum and vanadium to be within the ranges given or from | 0.30 to 2.00 |

The impurities, phosphorus and sulfur, will be .04 per cent. or under, and the iron content will be sufficient to make 100 per cent.

In addition to the above alloying elements uranium, in amounts of from 0.15 to 0.50 per cent. may be added, the amount of iron in the composition being correspondingly lessened. When used, the uranium will replace a corresponding amount of molybdenum or vanadium, or part of each of these two elements.

The carbon, manganese and silicon will be added to the bath in the furnace, and the molybdenum and vanadium additions preferably, although not necessarily, will be made in the ladle. When used, the uranium will be added to the metal in the ladle.

In making my improved steel alloy, ferro-alloys of silicon, manganese, molybdenum, vanadium and uranium will be found best for use.

The advantages of my invention result from the use in a high silicon alloy of the molybdenum and vanadium with the other alloying elements within the range in proportions specified. Alloys made in accordance with my invention have very great resistance to crystallization or fatigue and are particularly well adapted for use as rock drills and similar percussive tools.

Many variations in the proportions of the alloying elements may be made without departing from my invention, as defined in the appended claims.

I claim—

1. A steel alloy containing from about 0.40 to about 1.00 per cent. carbon, from about 0.50 to about 1.50 per cent. manganese, from about 1.50 to about 2.50 per cent. silicon, and a combined molybdenum and vanadium content of up to about 2.00 per cent. said molybdenum content ranging from 0.15 to 1.50 per cent. and said vanadium ranging from 0.15 to .50 per cent.

2. A steel alloy containing from 0.40 to 1.00 per cent. carbon, from 0.50 to 1.50 per cent. manganese, and having from 1.50 to 2.50 per cent. silicon, 0.70 per cent. molybdenum and 0.70 per cent. vanadium alloyed therewith.

3. A steel alloy containing from 0.40 to 1.00 per cent. carbon, from 0.50 to 1.50 per cent. manganese, from 1.50 to 2.50 silicon, and a combined molybdenum and vanadium content of from 0.50 to 1.00 per cent. and having at least .15 per cent molybdenum or vanadium.

4. A steel alloy containing from .40 to 1.00 per cent. carbon, from .50 to 1.50 per cent. manganese, from 1.50 to 2.50 per cent. silicon, a combined molybdenum and vanadium content of from .50 to .70 per cent. and having at least .15 per cent. of molybdenum or vanadium.

In testimony whereof, I have hereunto signed my name.

LINWOOD M. BROWN.